US006260427B1

United States Patent
Jones et al.

(10) Patent No.: US 6,260,427 B1
(45) Date of Patent: *Jul. 17, 2001

(54) DIAGNOSTIC RULE TOOL CONDITION MONITORING SYSTEM

(75) Inventors: Joel W. Jones, Windsor (CA); Ya Wu, Wuhan (CH)

(73) Assignee: Tri-Way Machine Ltd., Ontario (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/200,017

(22) Filed: Nov. 25, 1998

Related U.S. Application Data

(63) Continuation-in-part of application No. 08/901,609, filed on Jul. 28, 1997.

(51) Int. Cl.⁷ .................................................. G01N 19/00
(52) U.S. Cl. ............................................................ 73/865.9
(58) Field of Search .............................. 73/865.8, 865.9; 340/679, 680

(56) References Cited

U.S. PATENT DOCUMENTS

| | | | |
|---|---|---|---|
| 3,694,637 | 9/1972 | Edwin et al. | 235/151 |
| 4,207,567 * | 6/1980 | Juengel et al. | 340/680 |
| 4,351,029 | 9/1982 | Maxey et al. | 364/511 |
| 4,658,245 | 4/1987 | Dye et al. | 340/683 |
| 4,748,554 | 5/1988 | Gebauer et al. | 364/474 |
| 4,816,822 * | 3/1989 | Vache et al. | 340/825.15 |
| 5,070,655 * | 12/1991 | Aggarwal | 451/5 |
| 5,210,704 | 5/1993 | Husseiny | 364/551 |
| 5,247,452 | 9/1993 | Ueda et al. | 364/474 |
| 5,251,144 | 10/1993 | Famamurthi | 364/474 |
| 5,407,265 | 4/1995 | Hamidieh et al. | 340/680 |
| 5,566,092 | 10/1996 | Wang et al. | 364/551 |
| 5,587,931 | 12/1996 | Jones et al. | 364/551 |
| 5,921,726 * | 7/1999 | Shiozaki et al. | 408/6 |

* cited by examiner

*Primary Examiner*—Max Noori
(74) *Attorney, Agent, or Firm*—Reising, Ethington, Barnes, Kisselle, Learman & McCulloch, P.C.

(57) ABSTRACT

A tool condition monitoring system monitors the power consumption of a tool during performance of a cyclical task. The system monitors a plurality of characteristics of the power consumption and diagnoses the condition of the tool based upon the plurality of characteristics. A rule base of the plurality of characteristics is generated in a learning mode by acquiring a tool of known condition for a plurality of cycles. In monitor mode, the system monitors the power consumption of a tool and diagnosis the condition of the tool by indexing the rule base based upon the plurality of characteristics monitored. In addition, a method is disclosed wherein the band may be modified for accommodating tool wear and avoiding nuisance detection such that the system can keep monitoring in tool's lifetime.

13 Claims, 26 Drawing Sheets

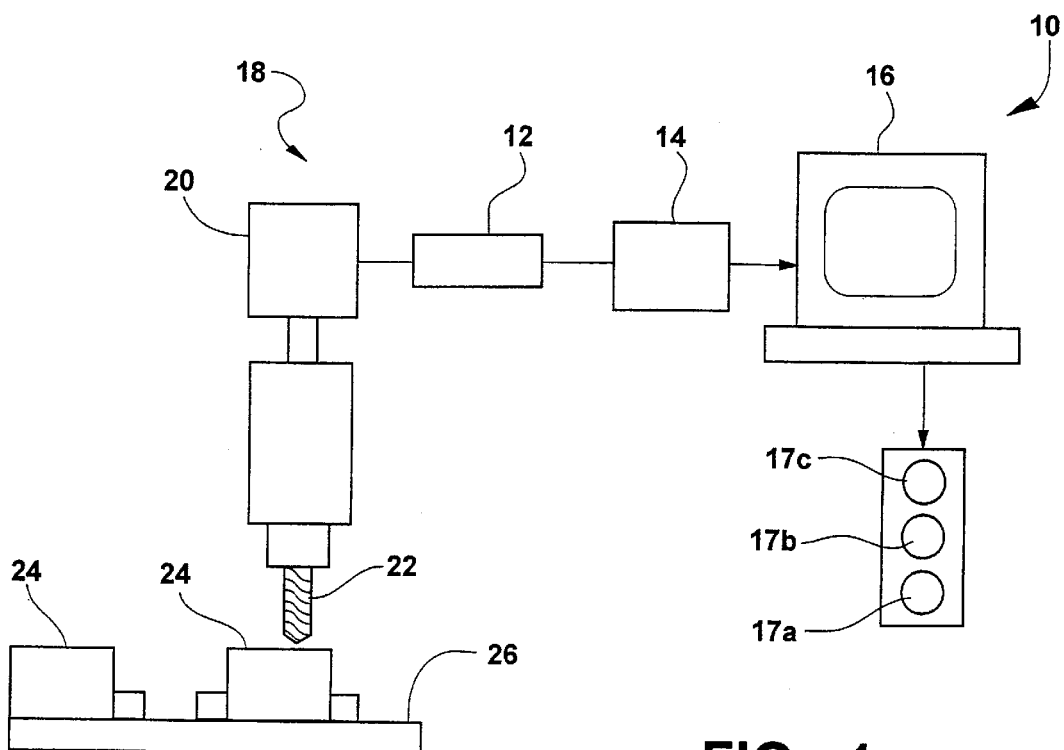
FIG - 1
FIG - 2
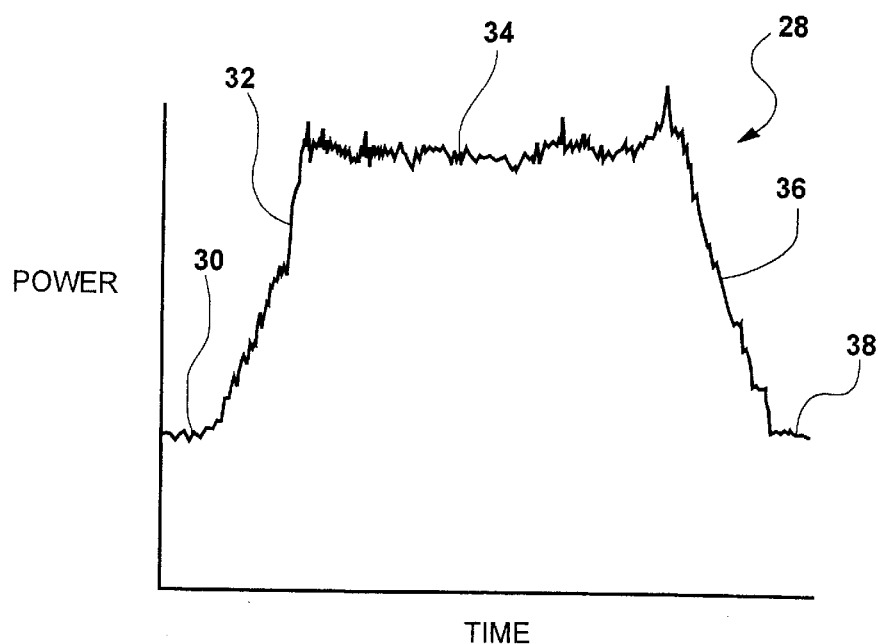

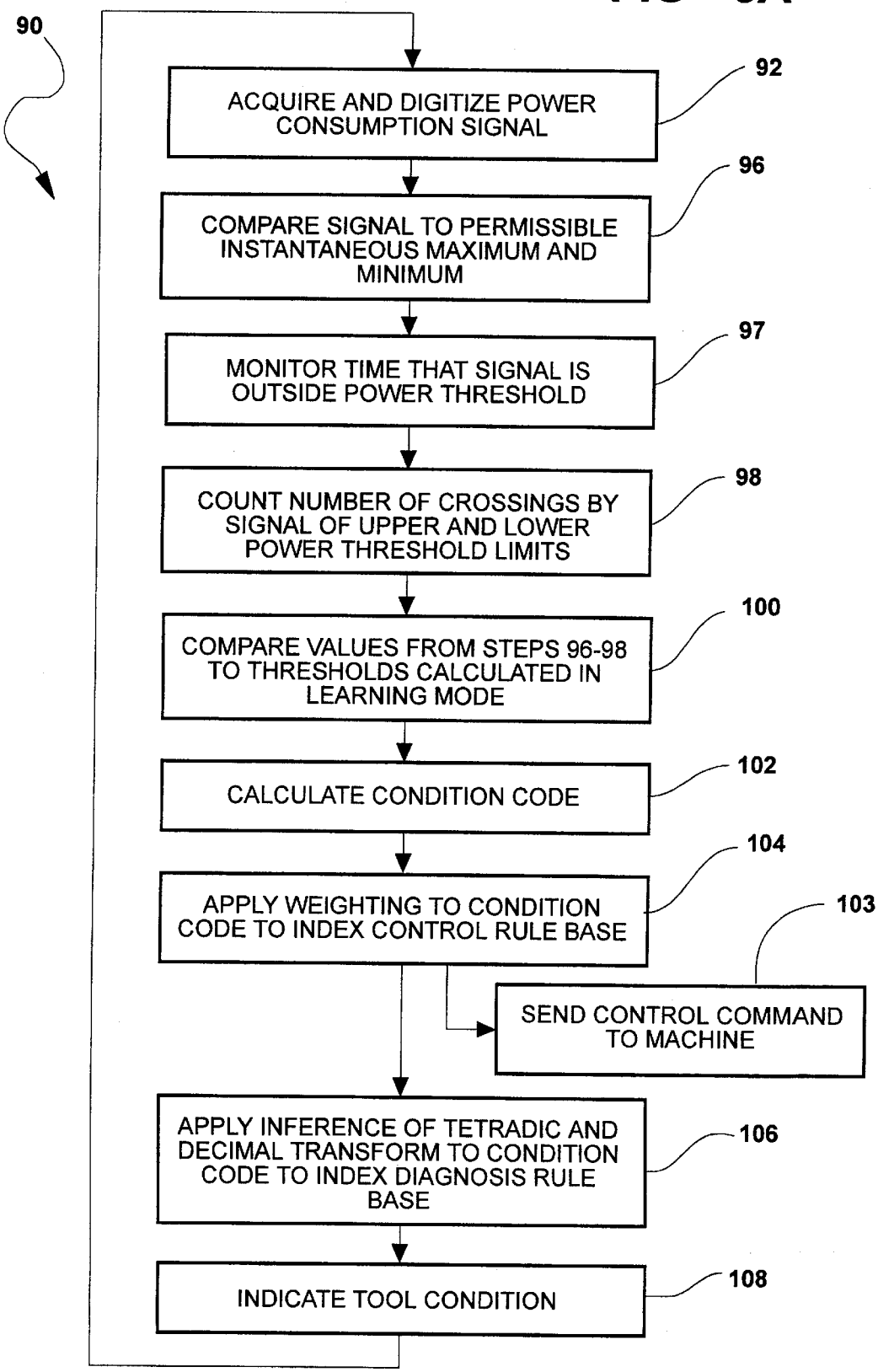

FIG - 7    Rules of cutting process monitoring

| No. | Code cr | Code cc | Code ma | Example of signal behavior | Typical features of signal | Possible reasons | Alarm light | Stop? |
|---|---|---|---|---|---|---|---|---|
| 1 | 0 | 0 | 0 | | • small amplitude<br>• stable process<br>• no instantaneous fast change(s) | normal | green | |
| 2 | 0 | 0 | 1 | | • instantaneous fast downward (underload) change(s) | • tool loosen or dropping<br>• workpiece loosen or moving | red | ✓ |
| 3 | 0 | 0 | 2 | | • instantaneous fast upward (overload) change(s) | • collision in somewhere<br>• tool chip or breakage<br>• hard spot(s) in material | red | ✓ |
| 4 | 0 | 0 | 3 | | instantaneous fast downward (underload) and upward (overload) change(s) | • collision or impact in somewhere<br>• tool chip or breakage<br>• tool loosen or dropping<br>• workpiece loosen or moving<br>• nonsmooth feeding/moving | red | ✓ |

FIG - 8

| | | | | |
|---|---|---|---|---|
| 5 | 0 1 0 | [waveform] | • downward(underload) unstable<br>• no instantaneous fast change(s) | • tool loosen or dropping<br>• workpiece loosen or moving<br>• porous or soft layer(s) in material<br>• tool missing or tool(s) missing material<br>• wrong size(smaller) tool(s)<br>• brand new tool(s) or fresh cutting edge(s)<br>• underload for any reason | yellow |
| 6 | 0 1 1 | [waveform] | • instantaneous fast downward (underload) change(s)<br>• downward(underload) unstable | • tool loosen or dropping<br>• workpiece loosen or moving<br>• porous or soft layer(s) in material<br>• tool missing or tool(s) missing material<br>• wrong size(smaller) tool(s)<br>• brand new tool(s) or fresh cutting edge(s) | red ✓ |
| 7 | 0 1 2 | [waveform] | • instantaneous fast upward (overload) change(s)<br>• downward(underload) unstable | • collision in somewhere<br>• tool chip or breakage<br>• hard spot(s) in material<br>• tool loosen or dropping<br>• workpiece loosen or moving<br>• tool missing or tool(s) missing material<br>• wrong size(smaller) tool(s)<br>• brand new tool(s) or fresh cutting edge(s) | red ✓ |
| 8 | 0 1 3 | [waveform] | • instantaneous fast downward (underload) and upward (overload) change(s)<br>• downward(underload) unstable | • collision or impact in somewhere<br>• tool chip or breakage<br>• tool loosen or dropping<br>• workpiece loosen or moving<br>• tool missing or tool(s) missing material<br>• wrong size(smaller tool(s)<br>• brand new tool(s) or fresh cutting edge(s) | red ✓ |

FIG - 9

| | | | | | |
|---|---|---|---|---|---|
| 9 | 0 | 2 | 0 | ![signal] | • upward(overload) unstable<br>• no instantaneous fast change(s) | • tool wear/worse/dull<br>• part of tools wear/worse/dull<br>• workpiece loosen or moving<br>• hard layer(s) in material<br>• wrong size(bigger) tool(s)<br>• overload for any reason | yellow | |
| 10 | 0 | 2 | 1 | ![signal] | • instantaneous fast downward (underload) change(s)<br>• upward(overload) unstable | • tool wear/worse/dull<br>• workpiece loosen or moving<br>• tool loosen or dropping<br>• hard layer(s) in material<br>• wrong size(bigger) tool(s)<br>• overload for any reason | red | ✓ |
| 11 | 0 | 2 | 2 | ![signal] | • instantaneous fast upward (overload) change(s)<br>• upward(overload) unstable | • collision in somewhere<br>• tool chip or breakage<br>• hard spot(s) in material<br>• tool(s) wear/worse/dull<br>• workpiece loosen or moving<br>• hard layer(s) in material<br>• wrong size(bigger) tool(s)<br>• overload for any reason | red | ✓ |
| 12 | 0 | 2 | 3 | ![signal] | • instantaneous fast downward (underload) and upward (overload) change(s)<br>• upward(overload) unstable | • collision or impact in somewhere<br>• tool chip or breakage<br>• tool wear/worse/dull<br>• workpiece loosen or moving<br>• tool loosen or dropping<br>• hard layer(s) in material<br>• wrong size(bigger) tool(s)<br>• overload for any reason | red | ✓ |
| 13 | 0 | 3 | 0 | ![signal] | • downward(underload) and upward(overload) unstable<br>• no instantaneous fast change(s) | • tool wear/worse/dull<br>• un-homogeneous material<br>• abnormal cutting cycle<br>• tool loosen or dropping<br>• workpiece loosen or moving | yellow | |

FIG - 10

| | | | | | |
|---|---|---|---|---|---|
| 14 | 0 | 3 | 1 | graph | • instantaneous fast downward (underload) change(s)<br>• downward(underload) and upward(overload) unstable | • tool wear/worse/dull<br>• tool loosen or dropping<br>• workpice loosen or moving<br>• tool missing or tool missing material<br>• un-homogenous material<br>• abnormal cutting cycle | red ∨ |
| 15 | 0 | 3 | 2 | graph | • instantaneous fast upward (overload) change(s)<br>• downward(underload) and upward(overload) unstable | • collision in somewhere<br>• tool chip or breakage<br>• tool wear/worse/dull<br>• tool loosen or dropping<br>• workpiece loosen or moving<br>• hard layer(s) in material<br>• abnormal cutting cycle | red ∨ |
| 16 | 0 | 3 | 3 | graph | • instantaneous fast downward (underload) and upward (overload) change(s)<br>• downward(underload) and upward(overload) unstable | • collision or iimpact in somewhere<br>• tool chip or breakage<br>• tool wear/worse/dull<br>• tool loosen or dorpping<br>• workpiece loosen or moving<br>• un-homogeneous material<br>• abnormal cutting cycle | red ∨ |
| 17 | 1 | 0 | 0 | graph | • level downward(underload)<br>• stable process<br>• no instantaneous fast change(s) | • a little underload<br>• brand new tool(s) or fresh cutting edge(s)<br>• wrong size(smaller) tool(s)<br>• tool missing or toll missing material<br>• soft material<br>• tool loosen or dropping<br>• workpece loosen or moving | yellow |

FIG - 11

| | | | | | | |
|---|---|---|---|---|---|---|
| 18 | 1 | 0 | 1 | [waveform] | • instantaneous fast downward (underload) change(s)<br>• level downward(underload) | • brand new tool(s) or fresh cutting edge(s)<br>• tool missing or tool missing material<br>• tool loosen or dropping<br>• workpiece loosen or moving<br>• wrong size(smaller) tool(s)<br>• soft material | red ∨ |
| 19 | 1 | 0 | 2 | [waveform] | • instantaneous fast upward (overload) change(s)<br>• level downward(underload) | • collision in somewhere<br>• tool chip or breakage<br>• brand new tool(s) or fresh cutting edge(s)<br>• tool missing or tool missing material<br>• tool loosen or dropping<br>• workpiece loosen or moving<br>• hard spot(s) in material<br>• wrong size(smaller) tool(s) | red ∨ |
| 20 | 1 | 0 | 3 | [waveform] | • instantaneous fast downward (underload) and upward (overload) change(s)<br>• level downward(underload) | • collision or impact in somewhere<br>• tool chip or breakage<br>• brand new tool(s) or fresh cutting edge(s)<br>• tool missing or tool missing material<br>• tool loosen or dropping<br>• workpiece loosen or moving<br>• underload for any reason<br>• wrong size tool(s) | red ∨ |
| 21 | 1 | 1 | 0 | [waveform] | • level downward(underload)<br>• downward(underload) unstable<br>• non instantaneous fast change(s) | • typical underload<br>• brand new tool(s) or fresh cutting edge(s)<br>• wrong size(smaller) tool(s)<br>• tool missing or tool missing material<br>• tool loosen or dropping<br>• workpiece loosen or moving<br>• porous or sfot layer(s) in material | yellow |

FIG - 12

| | | | | | | |
|---|---|---|---|---|---|---|
| 22 | 1 | 1 | 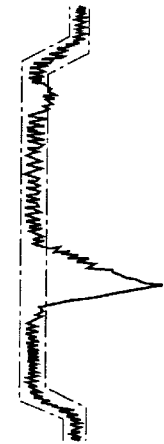 | • level downward(underload)<br>• downward(underload)<br>• unstable<br>• instantaneous fast downward (underload) change(s) | • typical underload<br>• tool loosen or dropping<br>• workpiece loosen or moving<br>• tool missing or tool missing material<br>• brand new tool(s) or fresh cutting edge(s)<br>• wrong size(smaller) tool(s)<br>• abnormal cutting cycle<br>• porous or soft layer(s) in material | red | ⟩ |
| 23 | 1 | 1 | 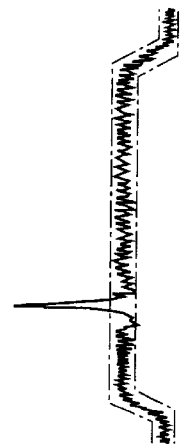 | • level downward(underload)<br>• downward(underload)<br>• unstable<br>• instantaneous fast upward (overload) change(s) | • collision in somewhere<br>• tool chip or breakage<br>• hard spot(s) in material<br>• tool loosen or dropping<br>• workpiece loosen or moving<br>• tool missing or tool missing material<br>• brand new tool(s) or fresh cutting edge(s)<br>• wrong tool(s)<br>• un-homogeneous material | red | ⟩ |
| 24 | 1 | 1 |  | • level downward(underload)<br>• downward(underload)<br>• unstable<br>• instantaneous fast downward (underload) and upward (overload) change(s) | • collision or impact in somewhere<br>• tool chip or breakage<br>• tool loosen or dropping<br>• workpiece loosen or moving<br>• tool missing or tool missing material<br>• brand new tool(s) or fresh cutting edge(s)<br>• wrong tool(s)<br>• un-homogeneous material | red | ⟩ |

FIG - 13

| 25 | 1 | 2 | 0 | [waveform] | • level downward(underload)<br>• upward(overload) unstable<br>• no instantaneous fast change(s) | • unstable process<br>• tool(s) is becoming dull or part of tool(s) is worn<br>• brand new tool(s) or fresh cutting edge(s)<br>• tool missing or tool missing material<br>• tool loosen or dropping<br>• workpiece loosen or moving<br>• hard layer(s) in material<br>• wrong size tool(s) | yellow | ✓ |
|---|---|---|---|---|---|---|---|---|
| 26 | 1 | 2 | 1 | [waveform] | • level downward(underload)<br>• upward(overload) unstable<br>• instantaneous fast downward (underload) change(s) | • tool missing or tool missing material<br>• tool loosen or dropping<br>• workpiece loosen or moving<br>• tool wear/worse/dull<br>• brand new tool(s) or fresh cutting edge(s)<br>• wrong tool(s)<br>• abnormal cutting cycle | red | ✓ |
| 27 | 1 | 2 | 2 | [waveform] | • level downward(underload)<br>• upward(overload) unstable<br>• instantaneous fast upward (overload) change(s) | • collision in somewhere<br>• tool chip or breakage<br>• hard layer(s) in material<br>• tool missing or tool missing material<br>• tool loosen or dropping<br>• workpiece loosen or moivng<br>• tool wear/worse/dull<br>• brand new tool(s) or fresh cutting edge(s)<br>• wrong tool(s) | red | ✓ |

FIG - 14

| | | | | | | | |
|---|---|---|---|---|---|---|---|
| 8 | 1 | 2 | 3 | [waveform] | • level downward(underload)<br>• upward(overload) unstable<br>• instantaneous fast downward (underload) and upward (overload) change(s) | • collision or impact in somewhwere<br>• tool chip or breakage<br>• hard layer(s) in material<br>• tool missing or tool missing material<br>• tool loosen or dropping<br>• workpiece loosen or moving<br>• tool wear/worse/dull<br>• brand new tool(s) or fresh cutting edge(s)<br>• wrong tool(s) | red | ⟩ |
| 29 | 1 | 3 | 0 | [waveform] | • level downward(underload)<br>• downward(underload) and upward(overload) unstable<br>• no instantaneous fast change(s) | • unstable process<br>• tool(s) is becoming dull or part of tool(s) is worn<br>• brand new tool(s) or fresh cutting edge(s)<br>• tool missing or tool missing material<br>• tool loosen or dropping<br>• workpiece loosen or moving<br>• un-homogeneous material<br>• wrong size tool(s) | red | ⟩ |
| 30 | 1 | 3 | 1 | [waveform] | • level downward(underload)<br>• downward(underload) and upward(overload) unstable<br>• instantaneous fast downward (underload) change(s) | • tool missing or tool missing material<br>• tool loosen or dropping<br>• workpiece loosen or moving<br>• tool wear/worse/dull<br>• brand new tool(s) or fresh cutting edge(s)<br>• wrong tool(s)<br>• non-homogeneous material<br>• abnormal cutting cycle | red | ⟩ |

FIG - 15

| | | | | | | |
|---|---|---|---|---|---|---|
| 31 | 1 | 3 | 2 | (waveform) | • level downward(underload)<br>• downward(underload) and upward(overload) unstable<br>• instantaneous fast upward (overload) change(s) | • collision in somewhere<br>• tool chip or breakage<br>• hard layer(s) in material<br>• brand new tool(s) or fresh cutting edge(s)<br>• tool missing or tool missing material<br>• tool loosen or dropping<br>• workpiece loosen or moving<br>• tool wear/worse/dull<br>• wrong tool(s)<br>• un-homogeneous material | red ↙ |
| 32 | 1 | 3 | 3 | (waveform) | • level downward(underload)<br>• downward(underload) and upward(overload) unstable<br>• instantaneous fast downward (underload) and upward (overload) change(s) | • collision or impact in somewhere<br>• tool chip or breakage<br>• hard layer(s) in material<br>• brand new tool(s) or fresh cutting edge(s)<br>• tool missing or tool missing material<br>• tool loosen or dropping<br>• workpiece loosen or moving<br>• tool wear/worse/dull<br>• wrong tool(s)<br>• un-homogeneous material | red ↙ |
| 33 | 2 | 0 | 0 | (waveform) | • level upward(overload)<br>• stable process<br>• no instantaneous fast change(s) | • tool wear/worse/dull<br>• workpiece loosen or moving<br>• hard material<br>• wrong size(bigger) tool(s)<br>• overload for any reason | yellow |

FIG - 16

| | | | | | | |
|---|---|---|---|---|---|---|
| 34 | 2 | 0 | 1 | 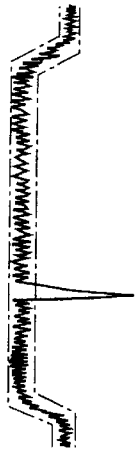 | • level upward(overload)<br>• instantaneous fast downward (underload) change(s) | • tool wear/worse/dull<br>• tool missing material<br>• workpiece loosen or moving<br>• tool loosen or dropping<br>• wrong size(bigger) tool(s)<br>• hard material<br>• overload for any reason | red ✓ |
| 35 | 2 | 0 | 2 | 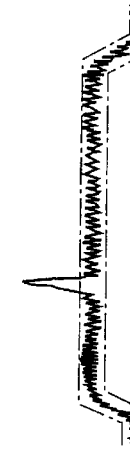 | • level upward(overload)<br>• instantaneous fast upward (overload) change(s) | • collision in somewhere<br>• tool chip or breakage<br>• tool wear/worse/dull<br>• hard material<br>• wrong size(bigger) tool(s)<br>• overload for any reason | red ✓ |
| 36 | 2 | 0 | 3 | 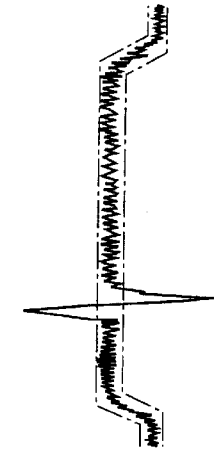 | • level upward(overload)<br>• instantaneous fast downward (underload) and upward (overload) change(s) | • collision or impact in somewhere<br>• tool chip or breakage<br>• tool wear/worse/dull<br>• workpiece loosen or moving<br>• tool loosen or dropping<br>• hard material<br>• wrong size(bigger) tool(s)<br>• overload for any reason | red ✓ |
| 37 | 2 | 1 | 0 | 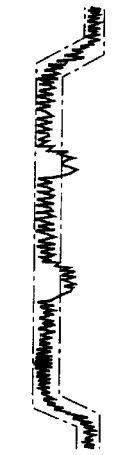 | • level upward(overload)<br>• downward(underload)<br>• unstable<br>• no instantaneous fast change(s) | • unstable process<br>• tool wear/worse/dull<br>• workpiece loosen or moving<br>• tool loosen or dropping<br>• tool missing or tool(s) missing material<br>• wrong size tool(s)<br>• brand new tool(s) or fresh cutting edge(s)<br>• un-homogeneous material | yellow |

FIG - 17

| | | | | | | |
|---|---|---|---|---|---|---|
| 38 | 2 | 1 | 1 | (waveform) | • level upward(overload)<br>• downward(underload)<br>• unstable<br>• instantaneous fast downward (underload) change(s) | • tool missing or tool(s) mising material<br>• tool loosen or dropping<br>• workpiece loosen or moving<br>• tool wear/worse/dull<br>• wrong tool(s)<br>• porous or soft layer(s) in material<br>• brand new tool(s) or fresh cutting edge(s)<br>• abnormal cutting cycle | red | √ |
| 39 | 2 | 1 | 2 | (waveform) | • level upward(overload)<br>• downward(underload)<br>• unstable<br>• instantaneous fast upward (overload) change(s) | • collision in somewhere<br>• tool chip or breakage<br>• hard spot(s) in material<br>• tool wear/worse/dull<br>• workpiece loose or moving<br>• tool loosen or dropping<br>• tool missing or tool(s) missing material<br>• wrong size(bigger) tool(s)<br>• hard material | red | √ |
| 40 | 2 | 1 | 3 | (waveform) | • level upward(overload)<br>• downward(underload)<br>• unstable<br>• instantaneous fast downward (underload) and upward (overload) change(s) | • collision or impact in somwhere<br>• tool chip or breakage<br>• tool wear/worse/dull<br>• workpiece loosen or moving<br>• overload for any reason<br>• tool loosen or dropping<br>• tool missing or toll(s) missing material<br>• hard material<br>• wrong size(bigger) tool(s) | red | √ |
| 41 | 2 | 2 | 0 | (waveform) | • level upward(overload)<br>• upward(overload) unstable<br>• no instantaneous fast change(s) | • typical overload<br>• tool wear/worse/dull<br>• hard material<br>• wrong size(bigger) tool(s)<br>• workpiece loosen or moving<br>• overload for any reason | yellow | |

FIG - 18

| | | | | | | |
|---|---|---|---|---|---|---|
| 42 | 2 | 1 | 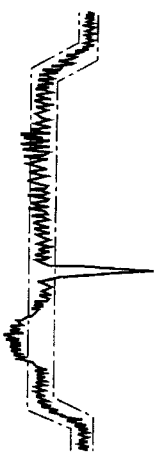 | • level upward(overload)<br>• upward(overload) unstable<br>• instantaneous fast downward (underload) change(s) | • tool wear/worse/dull<br>• hard material<br>• wrong size(bigger) tool(s)<br>• workpiece loosen or moving<br>• tool loosen or dropping<br>• overload for any reason | red ✓ |
| 43 | 2 | 2 | 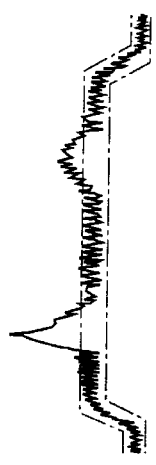 | • level upward(overload)<br>• upward(overload) unstable<br>• instantaneous fast upward (overload) change(s) | • typical overload<br>• collision in somewhere<br>• tool chip or breakage<br>• hard layer(s) in material<br>• tool wear/worse/dull<br>• workpiece loosen or moving<br>• wrong size(bigger) tool(s)<br>• hard material<br>• overload for any reason | red ✓ |
| 44 | 2 | 3 | 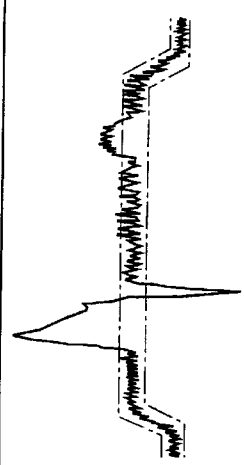 | • level upward(overload)<br>• upward(overload) unstable<br>• instantaneous fast downward (underload) and upward (overload) change(s) | • typical overload<br>• collision or impact in somewhere<br>• tool chip or breakage<br>• hard layer(s) in material<br>• tool wear/worse/dull<br>• workpiece loosen or moving<br>• wrong size(bigger) tool(s)<br>• hard material<br>• overload for any reason | red ✓ |
| 45 | 3 | 0 | 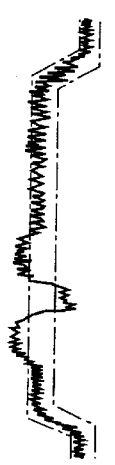 | • level upward(overload)<br>• downward(underload) and upward(overload) unstable<br>• no instantaneous fast change(s) | • typical overload<br>• tool wear/worse/dull<br>• non-homogeneous material<br>• wrong size(bigger) tool(s)<br>• workpiece loosen or moving<br>• overload for any reason<br>• abnormal cycle | red |

FIG - 19

| | | | | | | |
|---|---|---|---|---|---|---|
| 46 | 2 | 3 | 1 | [waveform] | • level upward(overload)<br>• downward(underload) and upward(overload) unstable<br>• instantaneous fast downward (underload) chage(s) | • tool wear/worse/dull<br>• workpiece loosen or moving<br>• tool loosen or dropping<br>• hard material<br>• wrong size(bigger) tool(s)<br>• overload for any reason<br>• abnormal cutting cycle | red | ⌄ |
| 47 | 2 | 3 | 2 | [waveform] | • level upward(overload)<br>• downward(underload) and upward(overload) unstable<br>• instantaneous fast upward (overload) change(s) | • collision in somewhere<br>• tool chip or breakage<br>• tool wear/worse/dull<br>• tool loosen or dropping<br>• workpiece loosen or moving<br>• hard layers in material<br>• wrong size(bigger) tool(s)<br>• overload for any reason<br>• un-homogeneous material<br>• abnormal cutting cycle | red | ⌄ |
| 48 | 2 | 3 | 3 | [waveform] | • level upward(overload)<br>• downward(underload) and upward(overload) unstable<br>• instantaneous fast downward (underload) and upward (overload) change(s) | • collision or impact in somewhere<br>• tool chip or breakage<br>• tool wear/worse/dull<br>• tool loosen or dropping<br>• workpiece loosen or moving<br>• wrong size(bigger) tool(s)<br>• overload for any reason<br>• un-homogeneous material<br>• abnormal cutting cycle | red | ⌄ |
| 49 | 3 | 0 | 0 | [waveform] | • big amplitude<br>• stable process<br>• no instantaneous fast change(s) | • dull tools<br>• strong vibration<br>• un-homogeneous material | yellow | |

FIG - 20

| | | | | | | |
|---|---|---|---|---|---|---|
| 50 | 3 | 0 | 1 | ~waveform~ | • big amplitude<br>• instantaneous fast downward (underload) change(s) | • dull tools<br>• strong vibration<br>• tool loosen or dropping<br>• workpiece loosen or moving<br>• tool missing or tool missing material | red | ✓ |
| 51 | 3 | 0 | 2 | ~waveform~ | • big amplitude<br>• instantaneous fast upward (overload) change(s) | • collision in somewhere<br>• tool chip or brakage<br>• dull tools<br>• strong vibration<br>• hard spot(s) in material | red | ✓ |
| 52 | 3 | 0 | 3 | ~waveform~ | • big amplitude<br>• instantaneous fast downward (underload) and upward (overload) change(s) | • collision or impact in somewhere<br>• tool chip or breakage<br>• tool loosen or dropping<br>• workpiece loosen or moving<br>• dul l tools<br>• strong vibration | red | ✓ |
| 53 | 3 | 1 | 0 | ~waveform~ | • big amplitude<br>• downward(underload) unstable<br>• no instantaneous fast change(s) | • dull tools<br>• strong vibration<br>• tool loosen or dropping<br>• workpiece loosen or moving<br>• tool missing or tool(s) missing material<br>• wrong size(smaller) tool(s)<br>• brand new tool(s) or fresh cutting edge(s)<br>• un-homogenous material | red | |

FIG-21

| | | | | | | |
|---|---|---|---|---|---|---|
| 54 | 3 | 1 | 1 | ~graph~ | • big amplitude<br>• downward(underload)<br>• unstable<br>• instantaneous fast downward (underload) change(s) | • tool loosen or dropping<br>• workpiece loosen or moving<br>• tool missing or tool(s) missing<br>• dull tools<br>• strong vibration<br>• wrong size(smaller) tool(s)<br>• brand new tool(s) or fresh cutting edge(s)<br>• porous or soft layer(s) in material<br>• abnormal cutting cycle | red | ✓ |
| 55 | 3 | 1 | 2 | ~graph~ | • big amplitude<br>• downward(underload)<br>• unstable<br>• instantaneous fast upward (overload) change(s) | • collision in somewhere<br>• tool chip or breakage<br>• tool loosen or dropping<br>• workpiece loosen or moving<br>• tool missing or toll(s) missing<br>• dull tools<br>• strong vibration<br>• wrong size(smaller) tool(s)<br>• brand new tools(s) or fresh cutting edge(s)<br>• hard spot(s) in material<br>• abnormal cutting cycle | red | ✓ |
| 56 | 3 | 1 | 3 | ~graph~ | • big amplitude<br>• downward(underload)<br>• unstable<br>• instantaneous fast downward (underload) and upward (overload) change(s) | • collision or impact in somewhere<br>• tool chip or breakage<br>• dull tools<br>• strong vibration<br>• tool loosen or dropping<br>• workpiece loosen or moving<br>• tool missing or tool(s) missing material<br>• brand new tool(s) or fresh cutting edge(s)<br>• abnormal cutting cycle | red | ✓ |

FIG - 22

| 57 | 3 | 2 | 0 |  | • big amplitude<br>• upward(overload) unstable<br>• no instantaneous fast change(s) | • dull tools<br>• strong vibration<br>• workpiece loosen or moving<br>• hard layer(s) in material<br>• wrong size(bigger) tool(s) | red | |
|---|---|---|---|---|---|---|---|---|
| 58 | 3 | 2 | 1 |  | • big amplitude<br>• upward(overload) unstable<br>• instantaneous fast downward (underload) change(s) | • workpiece loosen or moving<br>• tool loosen or dropping<br>• tool missing or tool missing material<br>• dull tools<br>• strong vibration<br>• hard layer(s) in material<br>• wrong size(bigger) tool(s)<br>• abnormal cutting cycle | red | ✓ |
| 59 | 3 | 2 | 2 |  | • big amplitude<br>• upward (overload) unstable<br>• instantaneous fast upward (overload) change(s) | • collision in somewhere<br>• tool chip or breakage<br>• dull tools<br>• strong vibration<br>• workpiece loosen or moving<br>• hard layer(s) in material<br>• wrong size(bigger) tool(s)<br>• overload for any reason<br>• abnormal cutting cycle | red | ✓ |
| 60 | 3 | 2 | 3 |  | • big amplitude<br>• upward (overload) unstable<br>• instantaneous fast downward (underload) and upward (overload) change(s) | • collision in somewhere<br>• tool chip or breakage<br>• dull tools<br>• strong vibration<br>• workpiece loosen or moving<br>• hard layer(s) in material<br>• wrong size(bigger) tool(s)<br>• overload for any reason<br>• abnormal cutting cycle | red | ✓ |

FIG - 23

| 61 | 3 | 3 | 0 |  | • big amplitude<br>• downward(overload) and upward(overload) unstable<br>• no instantaneous fast change(s) | • dull tools<br>• strong vibration<br>• tool loosen or dropping<br>• workpiece loosen or moving<br>• un-homogeneous material<br>• abnormal cutting cycle | red |  |
|---|---|---|---|---|---|---|---|---|
| 62 | 3 | 3 | 1 | 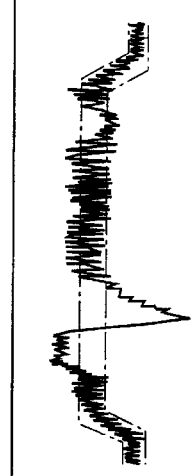 | • big amplitude<br>• downward(underload) and upward(overload) unstable<br>• instantaneous fast downward (underload) change(s) | • tool loosen or dropping<br>• workpiece loosen or moving<br>• tool missing or toll missing material<br>• dull tools<br>• strong vibration<br>• un-homogeneous material<br>• abnormal cutting cycle | red | ↘ |
| 63 | 3 | 3 | 2 | 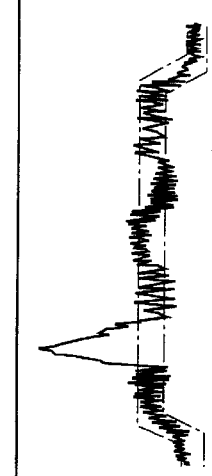 | • big amplitude<br>• downward(underload) and upward(overload) unstable<br>• instantaneous fast upward (overload) change(s) | • collision in somewhere<br>• tool chip or breakage<br>• dull tools<br>• strong vibration<br>• tool loosen or dropping<br>• workpiece loosen or moving<br>• un-homogeneous material<br>• abnormal cutting cycle | red | ↘ |
| 64 | 3 | 3 | 3 | 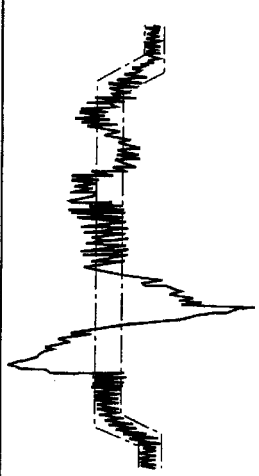 | • big amplitude<br>• downward(underload) and upward(overload) unstable<br>• instantaneous fast downward (underload) and upward (overload) change(s) | • collision or impact in somewhere<br>• tool loosen or dorpping<br>• dull tools<br>• strong vibration<br>• tool loosen or dropping<br>• workpiece loosen or moving<br>• tool missing or tool missing material<br>• un-homogeneous material<br>• abnormal cutting cycle | red | ↘ |

DIAGNOSTIC RULE TOOL CONDITION MONITORING SYSTEM

This application is a continuation-in-part of co-pending application Ser. No. 08/901,609 filed Jul. 28, 1997.

BACKGROUND OF THE INVENTION

The present invention relates to a tool monitoring system for monitoring the condition of an electric motor driven tool performing a cyclical operation.

Tool condition monitoring is one of the major concerns in modern machining operations, especially in machining operations for mass production. Failure to detect tool failure and wear leads to poor product quality and can even damage machine tools. On the other hand, a false detection of tool failure or wear may cause an unnecessary interruption of an entire production. Both can result in significant monetary loss.

Known tool monitoring systems include systems for "on-line tool condition monitoring." In on-line tool condition monitoring, the tool is monitored for defects after each cut or cycle. These tool monitoring systems typically use optical sensors or laser optical sensors which measure the geometry of the tool after each cut. However, on-line tool condition monitoring can only detect catastrophic failure of a tool after a cut and cannot monitor the gradual wear of a tool or predict the tool's failure. Further, these systems are vulnerable to chips, coolant, and environmental noises.

Other known methods for tool condition monitoring attempt to predict tool condition based on various sensor signals such as cutting force, acoustic emission, and vibration. However, sensors for monitoring cutting force are too expensive to use with multiple stations and multiple spindles. Acoustic emission and vibration sensors require additional wiring and are vulnerable to various noises.

Some monitoring systems monitor power consumption (or motor current) of the tool. As the tool wears (or if it fails) its power consumption changes. However, the power signals are complicated and the power signals to provide a reliable, accurate indication of it has proven difficult to use. The power signal does contain some "noise" due to factors other than tool condition. Typically, these systems set a range of signal that a monitored signal should fall within. When the monitored signal is outside this range, a worn tool or failure is indicated.

One major problem with monitoring the power consumption of the motor is that occasional spikes are experienced in a machine tool even under normal condition. The spikes can falsely indicate that the tool is worn. However, if the threshold is increased to prevent false signals, a worn tool may go undetected.

The inventors of the present invention previously developed a tool monitoring system which operates generally in two modes: learning mode and monitoring mode. In learning mode, the tool monitoring system gathers statistical data on the power consumption of tools of the selected tool type during learning cycles. A power threshold is generated based upon the statistical data. The tool monitoring system then counts the number of crossings by each of the learning cycles of the power threshold and generates statistical data regarding the number and value of crossings. Preferably, the mathematical operation of wavelet packet transform is used to calculate the power threshold. Feature wavelet packets of the power consumption signal of the tool are calculated. The power consumption signal is then reconstructed from the feature wavelet packets and used to determine the power threshold. In monitor mode, the tool monitoring system counts the number and value of crossings of the power threshold by the power consumption signal of a tool in operation. The tool monitoring system identifies a worn tool, or a tool breakage, or that an abnormal fault happened in the operation, when the number of crossings increases to certain numbers or a certain value relative to the crossings by the learning cycles. This previous invention was disclosed and claimed in U.S. Pat. No. 5,587,931 and application Ser. No. 08/901,609.

SUMMARY OF THE INVENTION

The present invention provides a real time tool monitoring system which continuously monitors a plurality of characteristics of the power consumption of the tool during operation in order to diagnose the condition of the tool and the likely cause of any problem.

The tool monitoring system of the present invention monitors a plurality of characteristics of the power consumption of the tool during performance of the cyclical task. The system diagnoses the condition of the tool based upon the plurality of characteristics of the power consumption, including the existence or absence of each of the plurality of characteristics.

Preferably, the system is first operated in a "learning mode," in which one or more tools of a known condition are acquired for a plurality of cycles. A plurality of characteristics of the power consumption of the known tools evaluated statistically in order to generate a plurality of threshold values.

First, a power threshold having an upper limit and a lower limit is generated based upon the average power consumption. The power threshold and average power consumption is a function of time over the cyclical task. During each cycle of the tool, the power consumption will cross the power threshold a plurality of times. Statistical information regarding the number of crossings by the power consumption of the upper and lower limits by the known tools is gathered to establish a threshold number of crossings of the upper limit and a threshold number of crossings of the lower limit.

Further, extreme high and low values, i.e. "spikes," in the power consumption are also monitored in the known tools and evaluated statistically to generate maximum and minimum permissible values. Again, this threshold is a function of time over the cyclical task.

The amount of time that the power consumption stays outside the power threshold, i.e. above the upper limit or below the lower limit, is also monitored statistically to generate a threshold time value.

The values gathered in the learning mode are then utilized to generate a diagnostic rule base which includes every possible combination of the plurality of characteristics monitored, i.e. number of crossings, maximum and minimum instantaneous values, and time outside threshold. Further, for each characteristic, there are four possibilities. First, the characteristic may be absent, i.e. the number of crossings has not been exceeded, the maximum and minimum permissible values have not been crossed and the time outside the threshold has not been exceeded. When the characteristic exists there are three more possibilities: the characteristic is occurring below the lower limit of the power threshold, above the upper limit of the power threshold or both above and below the power threshold. Thus, for the three characteristics monitored in the preferred embodiment, there are sixty four possible combinations which are associated with different tool conditions in the rule base.

In addition, certain machine operations may be able to utilize a worn tool. For a tooling operation that does not require the most extreme precision cutting, it may not be desirable to indicate a failed tool as rapidly as it would for other more precise cutting operations. Thus, it is desirable to have the thresholds be able to change during operation of the tool, as the tool experiences wear.

For this reason, in one variation of the present invention, the system monitors a plurality of characteristics, and certain combinations of characteristics are identified as relearning codes. If a relearning code is experienced, this is taken as an indication that the tool is experiencing some wear, but still may be capable of further use. When a relearning code is monitored, then several recent samples are utilized to relearn a band.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which:

FIG. 1 illustrates a tool monitoring system according to the present invention, monitoring the power consumption of a machine tool machining a series of work pieces.

FIG. 2 illustrates the power signal from one cycle of the machine tool as received by the tool monitoring system of FIG. 1.

FIG. 6A is a flow chart of the tool monitoring system of FIG. 1 in monitor mode.

FIG. 7 is a chart showing the diagnosis rule base for rules 1–4.

FIG. 8 is a chart of the diagnosis rule base of FIG. 7 for rules 5–8.

FIG. 9 is a chart of the diagnosis rule base of FIG. 7 for rules 9–13.

FIG. 10 is a chart of the diagnosis rule base of FIG. 7 for rules 14–17.

FIG. 11 is a chart of the diagnosis rule base of FIG. 7 for rules 18–21.

FIG. 12 is a chart of the diagnosis rule base of FIG. 7 for rules 22–24.

FIG. 13 is a chart of the diagnosis rule base of FIG. 7 for rules 25–27.

FIG. 14 is a chart of the diagnosis rule base of FIG. 7 for rules 28–30.

FIG. 15 is a chart of the diagnosis rule base of FIG. 7 for rules 31–33.

FIG. 16 is a chart of the diagnosis rule base of FIG. 7 for rules 34–37.

FIG. 17 is a chart of the diagnosis rule base of FIG. 7 for rules 38–41.

FIG. 18 is a chart of the diagnosis rule base of FIG. 7 for rules 42–45.

FIG. 19 is a chart of the diagnosis rule base of FIG. 7 for rules 46–49.

FIG. 20 is a chart of the diagnosis rule base of FIG. 7 for rules 50–53.

FIG. 21 is a chart of the diagnosis rule base of FIG. 7 for rules 54–56.

FIG. 22 is a chart of the diagnosis rule base of FIG. 7 for rules 57–60.

FIG. 23 is a chart of the diagnosis rule base of FIG. 7 for rules 61–64.

DETAILED DESCRIPTION OF A PREFERRED EMBODIMENT

Figure 3:
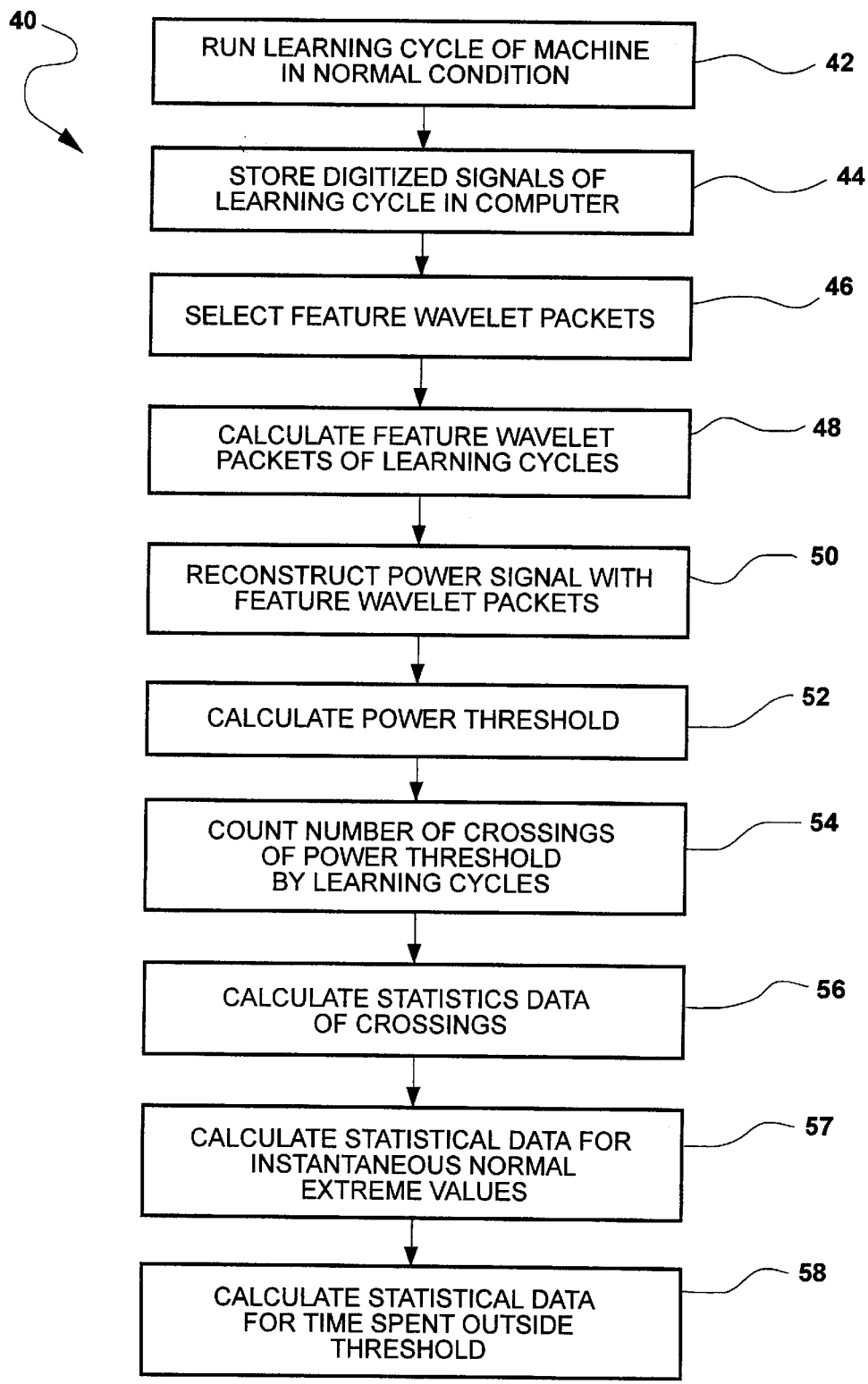
FIG. 3 is a flow chart of the tool monitoring system of FIG. 1 in its learning mode.

FIG. 1 shows a tool monitoring system 10 according to the present invention including a current transducer 12 connected to an analog-to-digital converter 14 and a CPU 16. The CPU 16 is also connected to a plurality of condition indicator lights 17a–c, which are preferably green, yellow and red, respectively. The tool monitoring system 10 is shown monitoring a machine tool 18 having an electric motor 20 driving a tool 22. For purposes of illustration, the machine tool 18 is shown machining a series of work pieces 24 being moved along a conveyor system 26. As will become apparent, the tool monitoring system 10 of the present invention can be used with any selected tool type using an electric motor and performing a repetitive, cyclical task.

In operation, the motor 20 and tool 22 are repeatedly loaded to cut each work piece 24, and then the conveyor system 26 positions another work piece 24 to the machine tool 18. The current transducer 12 continuously indicates the power consumption of the motor 20 by sending a power consumption signal to the analog-to-digital converter 14, which converts the power consumption signal into a format readable by the CPU 16. The analog-to-digital converter 14 sends a digital signal representing the amplitude of the power consumption signal at a series of current time segments. The digitized power consumption signal is stored in the CPU 16 and associated with its particular time segment, relative to the machine tool cycle.

FIG. 2 shows one cycle of the power consumption signal 28 of the machine tool 18 of FIG. 1, as received by the CPU 16. The machining operation is in the form of a cycle starting from tool engagement and ending with tool withdrawal. At the beginning of the cycle, the tool 22 is not engaging the work piece 24 and the power consumption signal 28 is at idling power 30. During the initial engagement 32 of the tool 22 with the work piece 24, the power consumption signal 28 rises. When the tool 22 is fully engaged in the work piece 24, the power consumption signal 28 reaches full engagement consumption 34. At full engagement 34, the power consumption signal 28 reaches a level and remains relatively unchanged, though there are fluctuations caused by various noise, such as cutting a hard spot in the work piece 24. Due to this fluctuation, it has been difficult to use a power signal to accurately predict tool condition. High "spikes" may occur in the signal occasionally even though the tool is not worn. After completion of machining the tool is withdrawn. During withdrawal 36 the power consumption signal 28 decreases steadily and finally returns to idling power 38.

As will be explained in detail below, the tool monitoring system 10 according to the present invention generally operates in two modes: a learning mode and a monitoring mode. In learning mode, the tool monitoring system 10 preferably receives data from several sample cycles of machine tools 18 of the selected tool type. Information related to the power consumption during each cycle run by each machine tool 18 is stored to develop expected signal ranges, or thresholds, and other statistical values. Then in monitoring mode, the tool monitoring system 10 compares the power consumption signal of a machine tool 18 with data gathered in the learning mode and diagnoses the condition of the machine tool 18 for each cycle. The determination is made by comparing the signal to the expected learning cycle, signal ranges, or thresholds and other statistical data gathered from tools of a known condition. Since the thresholds are developed by samples, they are more accurate than prior art "selected" thresholds.

FIG. 3 shows a flow chart for the learning mode 40 of the tool monitoring system 10 of FIG. 1. In learning mode 40, numerous learning cycles of a plurality of tools 22 of the selected tool type are run in 42. The tool 22 is selected to be a new tool or in normal condition. The power consumption signals 28 of the learning cycle are digitized by the analog-to-digital converter 14 and stored in the CPU 16 in 44.

The CPU 16 then selects feature components of the power consumption signal 28 in 46. In one preferred embodiment, wavelet transforms are used to break the signal into components, as explained in U.S. Pat. No. 5,587,931 entitled "Tool Condition Monitoring System" which is assigned to the assignee of the present invention and which is hereby incorporated by reference. In 46, the samples of the learning cycle are decomposed into different time-frequency components. The feature wavelet packets are selected from the components to represent the main information about the original power consumption signal 28, thereby the unwanted components of the power consumption signal 28, i.e. noise are filtered out from the signal.

In 50, the CPU 16 reconstructs the power consumption signal 28 of each learning cycle from the selected feature wavelet packets by the inverse of the function used to break the original power signal into components. The reconstructed power consumption signal 28 then contains sufficient information from the original power consumption signal 28, but with reduced noise. Notably, while only some of the learning cycles need be used to select the feature wavelet packets in step 46, preferably all of the learning cycles are used to develop data at step 50. The more cycles utilized, the more accurate the system.

In 52, the CPU 16 generates a power threshold based upon statistical data calculated at 50 from the learning cycles. The power threshold is a function of time over the machine tool cycle and includes an upper limit and a lower limit. The upper and lower limits are not the extremes of the signal, but rather some statistical function of the signal, preferably the average power consumption plus and minus five standard deviations, respectively. The learning cycle signals are expected to occasionally fall inside these thresholds.

In 56, the CPU 16 compares the power thresholds to the power consumption signals of the learning cycles. The CPU 16 compares each power consumption signal to the power thresholds at each time segment and counts the number of crossings by each power consumption signal. The crossings of the lower limit of the power threshold are preferably counted separately from the crossings of the upper limit of the power threshold. This is to say, the upper limit crossings are counted separately from lower limit crossings. Two means and two standard deviations would also be calculated separately.

In step 57, the CPU 16 calculates the statistical properties of occasional extreme high and low values of the power consumption. Preferably, an instantaneous maximum value is set at the average maximum value plus a certain number standard deviations and an instantaneous minimum value is set at the average minimum value minus a certain number standard deviations.

In step 58, the CPU 16 calculates the statistical properties of the amounts of time that the power consumption signals in the learning mode spend outside the power threshold, i.e. above the upper limit or below the lower limit. Preferably, a threshold time for the lower limit is calculated as the average time spent by power consumption signals below the lower limit plus a certain number standard deviations. Similarly, a threshold time for the upper limit is calculated as the average time spent by power consumption signals above the upper limit plus a certain number standard deviations.

Figure 4:
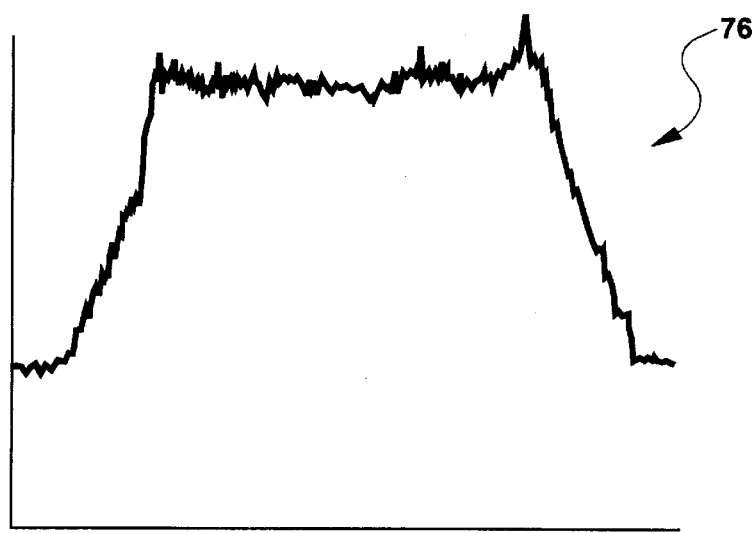
FIG. 4 is a reconstructed power consumption signal of FIG. 2, reconstructed from the feature wavelet packets selected from FIG. 4.

The reconstructed signal 76 of one of the learning cycles, created in step 50, is shown in FIG. 4. The CPU 16 performs the inverse wavelet packet transform on the feature wavelet packets, while setting the other packets to zero. Setting the other packets to zero eliminates unnecessary information end noise from the signal. The reconstructed signal 76 therefore comprises the principal components of the power consumption signal 28, without the unwanted components such as various noises.

Figure 5:
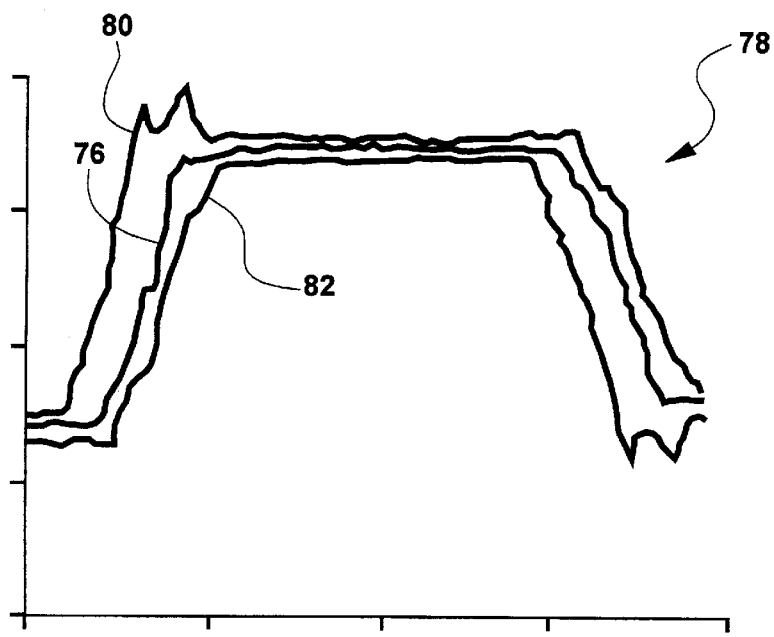
FIG. 5 is a power threshold based upon several reconstructed power consumption signals of the learning cycles.

The power threshold 78 created in step 52 is shown in FIG. 5. The power threshold 78 is based upon statistical properties from the reconstructed power consumption signals 76 from the learning cycles. The power threshold includes an upper limit 80 and a lower limit 82, which are both functions of time over the machine tool cycle. In this embodiment upper limit 80 and lower limit 82 are preferably calculated as plus and minus certain numbers standard deviations, respectively, from the mean of the reconstructed power consumption signals 76 of the learning cycles.

FIG. 5 also shows one of the power consumption signals 76 from the learning cycles. In learning mode 40, the CPU 16 compares the power consumption signal 76 from the learning cycles with the power threshold 78 to calculate means and standard deviations for number of crossings of the upper and lower limit 80, 82, time spent above the upper limit 80, time spent below the lower limit 82, and maximum and minimum instantaneous power consumption values. In practice, the power consumption signals from numerous learning cycles would be compared with the power threshold 78.

After creating a power threshold 78 and threshold values, the tool monitoring system 10 enters the monitoring mode 90, shown in FIG. 6A. In monitor mode 90, the tool monitoring system 10 is again connected to a machine tool 18 of the selected tool type as shown in FIG. 1. Preferably, the same CPU 16 is used in both the learning mode 40 and monitor mode 90. At this time, the power threshold 78 data have already been saved for the monitor mode. Moreover, it is preferred that the learning mode be performed at the actual work station where the CPU will be monitoring. Using the actual A/D converter 14 for the learning mode signal acquisition will insure that any individual characteristics of the motor, tool mounts, etc. will be accounted for in the thresholds.

In step 92 of monitor mode 90, the CPU 16 acquires and digitizes the power consumption signal of a machine tool 18 while the machine tool 18 performs its repetitive cyclical machining operations.

In step 96, the power consumption signal is compared to the instantaneous maximum and minimum values calculated in the learning mode. If the power threshold signal falls between the minimum and maximum values, then the value \_ma is set to equal 0. If the power consumption signal falls below the minimum value, \_ma is set to 1. If the maximum value is exceeded, then \_ma is set to equal 2. Finally, if the power consumption signal both exceeds the maximum value and falls below the minimum value, \_ma is set to 3.

In step 97, the CPU 16 monitors the time that the power consumption signal is outside the power threshold, i.e. above the upper power threshold 80 and below the lower threshold 82. In step 98, the CPU 16 counts the number of crossings by the power consumption signal of the upper and lower threshold limits 80, 82. In step 100, the values and numbers from steps 96, 97, 98 are compared to the threshold numbers. The times are compared to the threshold times. If the power consumption signal stays within the band, \_cc is set to 0. If the power consumption signal stays below the lower limit of the power threshold 82 longer than the threshold time for the lower limit of the power threshold calculated in the learning mode, then \_cc is set to 1. If the power consumption signal stays above the upper limit of the power threshold for time exceeding the threshold time for the upper limit of the power threshold calculated in the learning mode, then \_cc is set to 2. If both times are exceeded, \_cc is set to 3.

Also in step 100, the numbers of crossings are compared to the threshold numbers. If the number of crossings is less than the threshold numbers of crossings calculated in the learning mode, then \_cr is set to 0. If the number of crossings of the lower power threshold limit exceeds the threshold number of crossings of the lower threshold limit calculated in the learning mode, then \_cr is set to 1. If the number of crossings of the upper threshold limit exceeds the threshold number of crossings of the upper power threshold limit, then \_cr is set to 2. If both thresholds are exceeded, \_cr is set to 3.

In step 102, a condition code is calculated from the values for the three characteristics, \_cr, \_cc and \_ma. Preferably, the condition code is a three digit number of the three values, in the form \_cr \_cc \_ma. For example, if \_cr=3,\_cc=2 and \_ma=0, the condition code would be 320.

In step 103, the control rule base is indexed based upon a weighing of the condition code values, which will be described in detail below with respect to FIG. 6B. Based upon the condition code, the tool condition monitoring system 10 will turn on an appropriate condition indicator light 17a–d, and may send a control command to stop the machine in step 104.

In step 106, a different weighing is applied to the condition code utilizing an inference of tetradic and decimal transform. In the preferred embodiment, since each of the characteristics has one of four values, 0–3, each of the characteristics is multiplied by a different multiple of four. The value of \_cr is preferably multiplied by $4^2$, or 16. The value of \_cc is preferably multiplied by $4^1$, or 4. The value of \_ma is preferably multiplied by $4^0$, or 1. The results are then added to provide a unique decimal number for each possible combination of values for the three characteristics. In the preferred embodiment illustrated here, one is added to the resulting number to eliminate a zero value. It should be apparent that if more characteristics are utilized, higher multiples of four would be utilized. Further, the base number, in this case four, is equal to the number of possible values. The base number could be increased to accommodate more possible values. This technique is illustrated below:

$$\_cr*4^2+\_cc*4^1+\_ma*4^0+1=\text{Rule index}$$

$$\_cr*16+\_cc*4+\_ma*1+1$$

$$\_cr=0, \_cc=0, \_ma=0 \qquad \text{Example 1}$$

$$0*16+0*4+0*1+1=1$$

Therefore, diagnosis Rule 1 is indexed.

$$\_cr=1, \_cc=1, \_ma=0 \qquad \text{Example 2}$$

$$1*16+1*4+0*1+1=21$$

Therefore, diagnosis Rule 21 is indexed.

The Rule calculated using above method is then used to index a rule base in order to diagnose the condition of the machine tool 22. The tool condition is then indicated in step 108, such by a display on CPU 16 of text indicating the condition of the tool 22 and possible problems. The rule base will be described in detail below with respect to FIGS. 7–23.

It should be emphasized that the loop from 108 to 92 in FIG. 6A can be feedback in either scan-by-scan base (or point-by-point basis) or cycle-by-cycle base. If the loop goes can-by-scan, the system will immediately shut down machine in the cycle when any fault is detected. We call this as real-time monitoring. If the loop goes in cycle-by-cycle base, the system will shut down the machine after the cycle is finished even though the fault occurred in the cycle. This is called on-line monitoring.

Figure 6B:
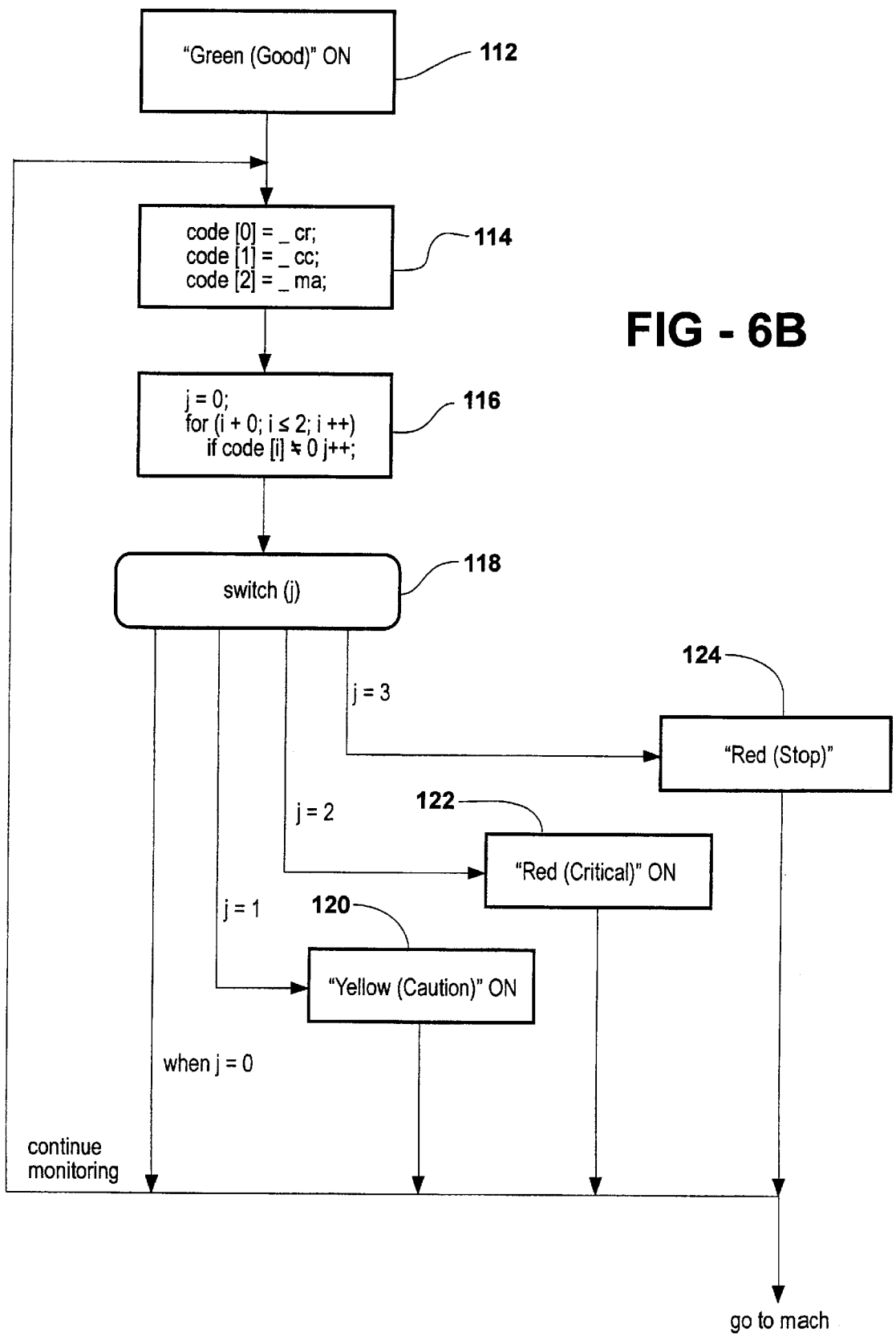
FIG. 6B is a flow chart of a control rule base for the tool monitoring system of FIG. 1 in monitor mode.

FIG. 6B shows the control chart 110 for weighing the condition code to index a control rule base. In step 112, the green light 17a (FIG. 1) is turned on. In step 114, the values of the three codes are put into an array called code. In step 116, the non-zero code is counted. If the code is 000, that is to say, no non-zero code is counted (j=0), the CPU 16 returns to step 114 to continue monitoring. When j=1, that is to say, there is one non-zero value in the codes, the yellow light 17b (FIG. 1) is turned on (see step 120). When j=2, meaning that there are two non-zero values in the codes, the red light of 17c (FIG. 1) is turned on (see step 122). When j=3, meaning that the three codes are non-zero, the red stop light 17d (FIG. 1) is turned on and the signal is at the same time sent to the machine control system to shut the machine down (see step 124).

The diagnosis rule base 130 is shown in FIGS. 7–23. As described above, the diagnosis rule base is indexed according to the possible values of the monitored characteristics \_cr, \_cc and \_ma. As can be seen in FIG. 7, if \_cr, \_cc and \_ma are all 0, Rule 1 is indexed, indicating that the tool is in a normal condition. If \_cr equals 0, \_cc equals 0, and \_ma equals 1, Rule 2 of rule base 130 is indexed, thereby indicating that either the tool or the work piece is loose and that the process should be stopped. The remaining Rules 3–64 are indexed in a similar manner according the weighing technique described above.

The tool condition monitoring system 10 of the present invention thus not only provides a warning of a worn or broken tool, but also diagnoses the present condition of the operation process based upon a plurality of characteristics of the power consumption signal.

Figure 24:
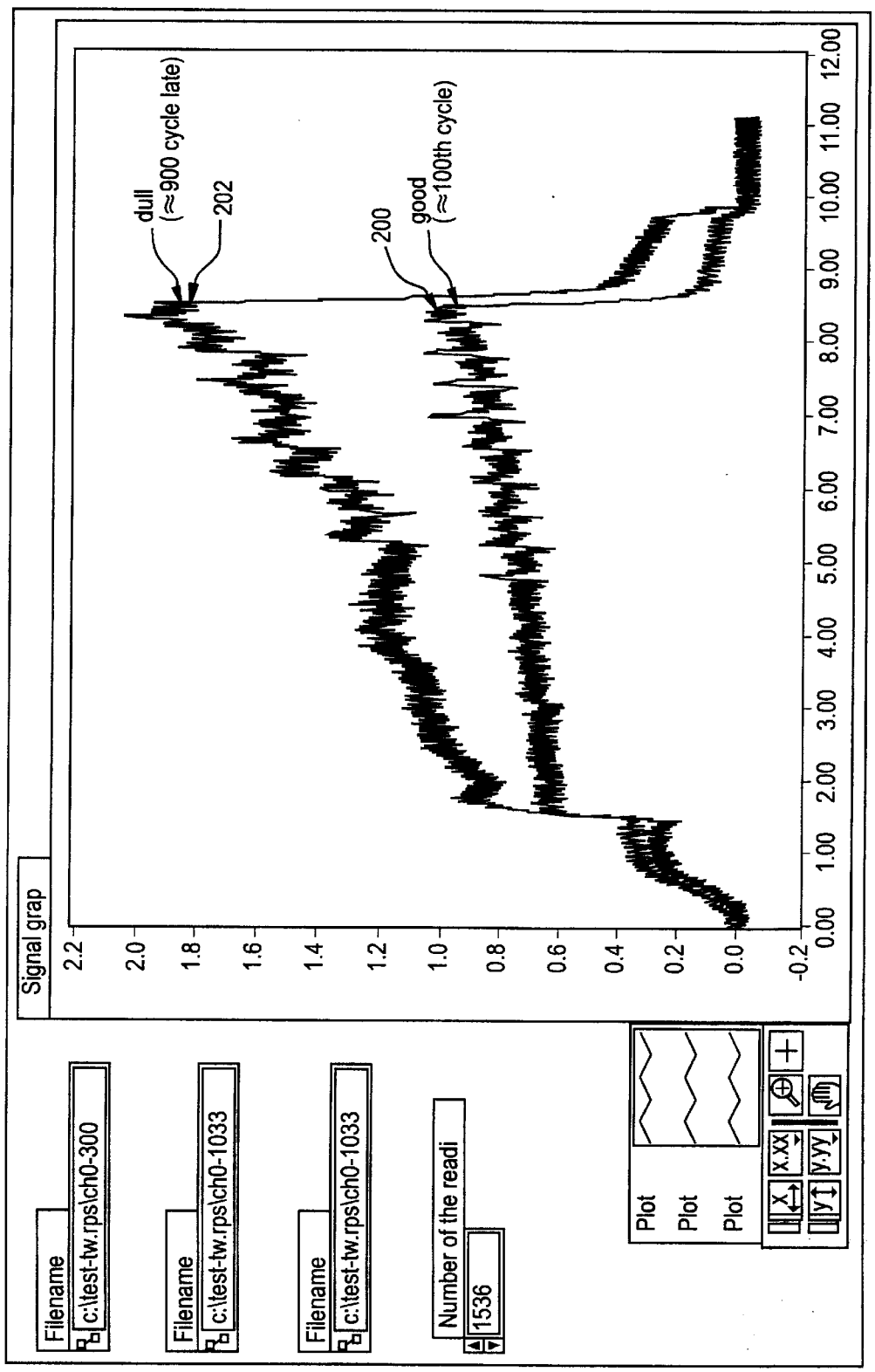
FIG. 24 shows a typical band for a new tool and a dull tool.

As shown in FIG. 24, a typical tooling cycle will generally have higher current values as the tool becomes worn. A cycle 200 is shown for a good or new tool, and a cycle 202 is shown for a dull tool. The above-described method of this invention might indicate that the tool at cycle 202 is ready for replacement. However, for certain machining operations it may be possible that tool 202 is still capable of further operation. Thus, the present invention adjusts the tolerance band as the tool wears. Simultaneously with adjustment of the tolerance band, the system will still monitor each cycle for certain combinations of conditions which will result in immediate stoppage of the tool.

Figure 25:
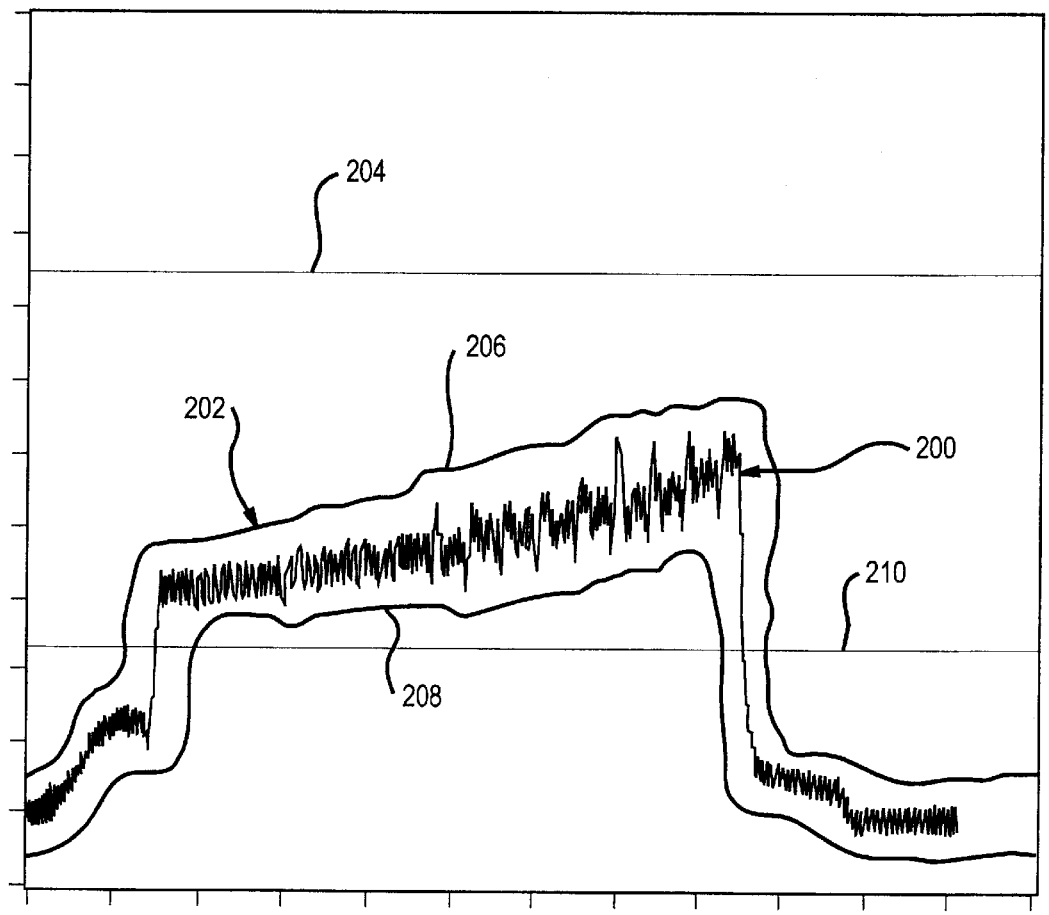
FIG. 25 shows the typical band for the new tool of FIG. 24 including the calculated tolerance band and limits.

As shown in FIG. 25, the cycle 200 for the good or new tool from FIG. 24 is shown with representative overlays of the calculated upper band tolerance 206 and the calculated lower band tolerance 208. Band 212 is defined between the tolerances 206 and 208 and is user set preferably as plus or minus certain number standard deviations. Additionally, an overall upper limit 204 and an overall lower limit 210 are displayed to provide a reference for how the tool is performing. As will be further described below, band 212 provides a high degree of control over the machine operation as a user defined number of previously acceptable cycles are used to calculate the upper 206 and lower 208 band tolerances. The system continues to monitor and compare each cycle of operation to band 212 and band 212 is maintained as the working band until a relearning code is detected.

Figure 26:
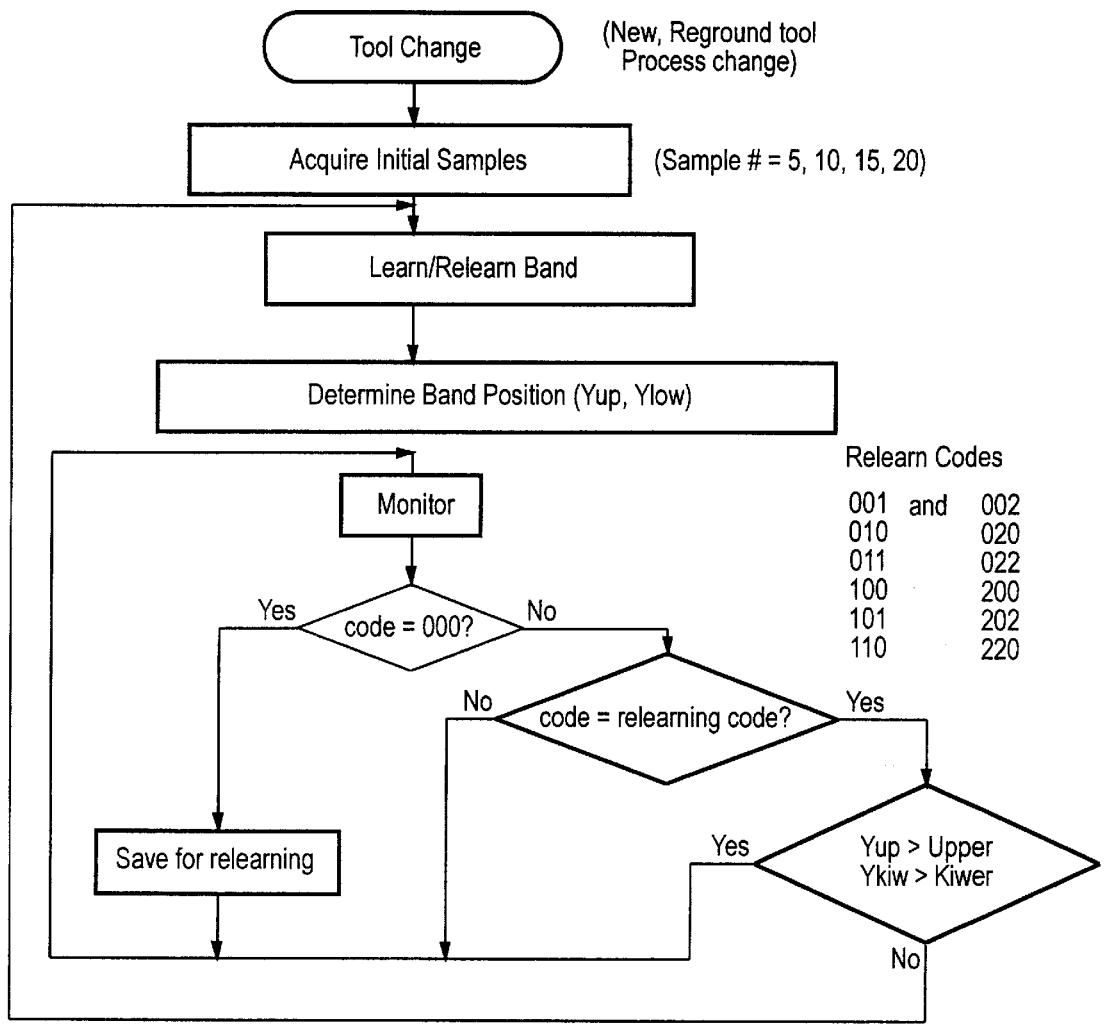
FIG. 26 is a flow chart of a variation of the present invention.

By varying the upper and lower tolerances 206,208 as the tool wears, the present invention determines minute changes in each cycle as normal tool wear is compensated for by the movement of band 212. As shown in FIG. 26, a flow chart of one method of the present invention is shown. When a tool is initially changed, samples are taken as with the above embodiments. The band 212, that is 206, 208 tolerances, are learned. The system then proceeds to monitor each cycle of operation. The results of that monitoring are detected. The detected results are compared to a code of 0,0,0, or a code which has no problem conditions. If the monitored code is at 0,0,0, then the particular cycle is saved as a relearning sample which will be utilized for relearning as the tool wears.

A user defined number of relearning codes continue to be stored to provide for later adjustment of band 212. The most recent 0,0,0 cycle is saved, and when the user defined number is reached, the most recent 0,0,0 cycle replaces the oldest 0,0,0 cycle. By this storage method the most recent and thus the most accurate cycles are used to recalculate the band 212.

If the code is not 0,0,0, then the next step is to compare the monitored code with a series of relearning codes. As shown in FIG. 26, there are a series of twelve codes which may be identified as relearning codes. If one of the relearning codes is monitored, then the upper 206 and lower 208 tolerances of band 212 are reset based upon the previously stored 0,0,0 cycle file samples.

Figure 27:
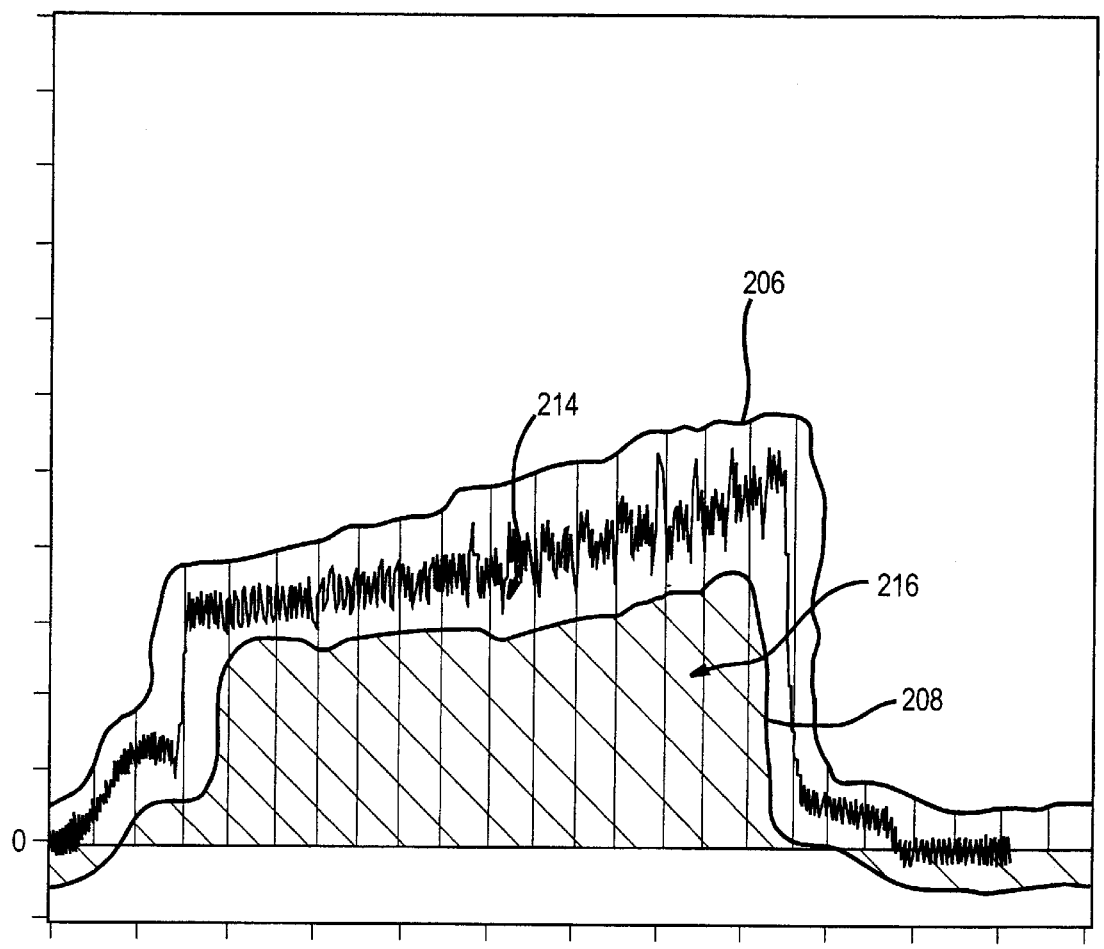
FIG. 27 shows the typical band for the new tool of FIG. 24 including the areas calculated to reposition the band.

As shown in FIG. 27 the upper 206 and lower 208 tolerances of band 212 are preferably repositioned based on the areas below the tolerance bands 206,208. The steady state of the machining operation is used as the zero or baseline to determine the repositioned working band position. The upper area 214 and the lower area 216 are individually compared with the average of the previously stored 0,0,0 cycle file samples. The upper 206 and lower 208 tolerances of band 212 are then adjusted by the difference between the initial band 212 position and the stored 0,0,0 cycle file samples.

As areas are used to calculate the repositioning of the tolerance band 212, overall band limits 204,210 (FIG. 25) can be based on the standard deviation of the overall area to provide an accurate indication of the overall limits of tool usage. These overall limits 204,210 are user defined and are preferably based on previous testing or manufacturer data. The overall limits 204,210 are thus defined by the acceptable standard deviation difference between the upper 206 and lower 208 tolerances of band 212. Although the overall upper limit 204 and the overall lower limit 210 are shown as horizontal lines in FIG. 25, this is for purposes of illustration. By providing horizontal limits the operator can pictorially relate and understand the position and movement of the working band 212 to the outer operational limits 204, 210.

After calculating the upper area 214 and the lower area 216, if the repositioned working band 212 exceeds the outer operational limits 204,210, the working band is prevented from exceeding the limit. In other words, the working band can never exceed the outer operational limits 204,210. The result of preventing the working band 212 from exceeding the outer operational limits 204,210 is the experience of a greater number of relearning codes. The machine can continue to be operated, however the continued experience of relearning codes is an indicator that a greater number of unacceptable parts are being produced. Thus, it is best that the machine be stopped and use of the current worn tool be discontinued as having exceeded extremes of proper operation.

In essence, the present invention looks to see if a relearning code is experienced. If so, then the system proceeds to relearn the working band within the extreme of the upper and lower limits based on recently captured acceptable cycles. In this way, the band position will move with tool wear and indicate minute changes in machine operation. Simultaneously, even if the monitored code is not a relearning code, the system still monitors each cycle for unacceptable conditions. Thus, detection results for each cycle are displayed and corrective measures, such as warning lights will be indicated. However, should an extreme problem occur during a cycle, the system will still shut down the machine. With this invention, applicants have found that very precise predictions of when a tool is about to break or fail are achieved. Still, the tool may be used beyond a time when wear is beginning, up till the time when its useful life is ended.

The foregoing description is exemplary rather than limiting in nature. Obviously, many modifications and variations of the present invention are possible in light of the above teachings. It is, therefore, to be understood that within the scope of the appended claims the invention may be practiced otherwise than as specifically described.

What is claimed is:

1. A method for monitoring the condition of an electric powered tool, comprising:

measuring a power consumption signal of the tool while performing a cyclical task;

analyzing selected feature components of the power consumption signal and establishing an initial power threshold tolerance band of predetermined value in a learning mode of the tool;

continuing to use the tool in a monitoring mode while performing the cyclic task and monitoring a plurality of selected feature components of the power consumption signal;

comparing the monitored power consumption signal with the initial power threshold tolerance band and based on the comparison, diagnosing the condition of the tool;

designating at least one combination of the plurality of selected feature components of the power consumption signal as a relearning code representative of a condition of tool wear; and during the monitoring of said power consumption signal, comparing the monitored power consumption signal to the relearning code and, in response to a detection that the monitored power consumption signal corresponds to said relearning code, recalculating and adjusting the initial power threshold tolerance band while operating in a relearning mode of the tool.

2. The method of claim 1 including using prior captured signal information to establish defined outer operational limits of an acceptable power threshold tolerance band.

3. The method of claim 2 wherein during the recalculation of the power threshold tolerance band, comparing the monitored signal information to the prior captured signal information to maintain the recalculated and adjusted power threshold tolerance band within the outer operational limits.

4. The method of claim 3 wherein the initial power threshold tolerance band has a corresponding area defined below the band, and wherein the recalculation of the band is made in relation to said area.

5. A method of monitoring a tool operation, comprising:

operating a tool in a learning mode while measuring defined operational characteristics of the tool;

analyzing the measured operational characteristics and calculating an initial operational tolerance band representative of a desired operating performance of the tool;

further operating the tool in a production mode while monitoring the operational characteristics of the tool;

designating at least certain operational characteristics as relearning code characteristics representative of a condition of the tool when experiencing tool wear;

while operating the tool in the production mode, comparing the monitored operational characteristics with the relearning code characteristics and, in response to detection that the monitored operational characteristics correspond to the relearning load characteristics, recalculating and adjusting the initial operational tolerance band in a relearning mode of the tool.

6. The method of claim 5 wherein the monitoring of the tool in the production and relearning modes includes monitoring a plurality of said operational characteristics.

7. The method of claim 6 wherein said operation characteristics of the tool measured in the learning mode includes a plurality of cycle codes representative of a operation cycle of the tool, and wherein said operational characteristics measured in said relearning mode are compared to said plurality of said cycle codes in said recalculation of said initial operational tolerance band.

8. The method of claim 7 including employing a user-defined quantity of said operation cycles for comparison in said relearning mode.

9. The method of claim 5 wherein the initial operational tolerance band includes upper and lower band limits and a defined area under said limits, and wherein said initial operational tolerance band is adjusted based on the difference between the initial position of said upper and lower band limits and said defined area and said plurality of said operation cycles.

10. The method of claim 5 wherein said initial operational tolerance band includes upper and lower band limits and including defined outer limits, and including controlling the adjustment of said initial operational tolerance band such that said band limits remain within said outer limits.

11. The method of claim 10 including calculating said outer limits based on a standard deviation of a calculated area below said upper and lower band limits.

12. The method of claim 10 including calculating said outer limits based on an acceptable standard deviation difference between said upper and lower band limits.

13. A method of monitoring a tool operation comprising the steps of:

1) operating said tool in a learning mode and capturing samples of selected operational characteristics associated with an operation cycle of said tool;

2) analyzing said capture sample characteristics to define an operational tolerance band having an upper limit and a lower limit of expected operation;

3) defining an extreme upper limit and an extreme lower limit relation to a standard deviation difference between said upper band limit and said lower band limit;

4) operating said tool in a production mode;

5) capturing selected operational characteristics of each operational cycle of said tool during said production mode;

6) storing some of said captured operational characteristics to define relearning code characteristics of said tool;

7) comparing said captured operational characteristics of each operational cycle to said stored relearning code characteristics; and 8) adjusting said upper band limit and said lower band limits within said extreme upper and lower limits should said captured operational characteristics match said relearning code characteristics.

* * * * *

UNITED STATES PATENT AND TRADEMARK OFFICE
CERTIFICATE OF CORRECTION

PATENT NO. : 6,260,427 B1
DATED : July 17, 2001
INVENTOR(S) : Joel W. Jones et al.

It is certified that error appears in the above-identified patent and that said Letters Patent is hereby corrected as shown below:

Title page, Item [54] and Column 1, line 1,
Change "DIAGNOSTIC RULE TOOL CONDITION MONITORING SYSTEM" to -- TRACK BAND TOOL CONDITION MONITORING SYSTEM --.

Column 6,
Line 29, change "end" to -- and --.

Column 8,
Lines 32 and 33, change "We call this as" to -- This is called --.

Signed and Sealed this

Fourteenth Day of May, 2002

*Attest:*

JAMES E. ROGAN
*Attesting Officer*   *Director of the United States Patent and Trademark Office*